(12) United States Patent  
Xiao

(10) Patent No.: US 11,696,952 B2  
(45) Date of Patent: Jul. 11, 2023

(54) NANOCAPSULE-BASED OCULAR THERAPY

(71) Applicant: LUTRONIC VISION INC., Burlington, MA (US)

(72) Inventor: Zhen Xiao, Beijing (CN)

(73) Assignee: LUTRONIC VISION INC., Burlington, MA (US)

( * ) Notice: Subject to any disclaimer, the term of this patent is extended or adjusted under 35 U.S.C. 154(b) by 500 days.

(21) Appl. No.: 16/639,848

(22) PCT Filed: Aug. 17, 2017

(86) PCT No.: PCT/CN2017/097834  
§ 371 (c)(1),  
(2) Date: Feb. 18, 2020

(87) PCT Pub. No.: WO2019/033336  
PCT Pub. Date: Feb. 21, 2019

(65) Prior Publication Data  
US 2020/0360515 A1     Nov. 19, 2020

(51) Int. Cl.  
*A61K 41/00*     (2020.01)  
*A61K 9/51*     (2006.01)  
(Continued)

(52) U.S. Cl.  
CPC ........ *A61K 41/0028* (2013.01); *A61K 9/0019* (2013.01); *A61K 9/0048* (2013.01);  
(Continued)

(58) Field of Classification Search  
CPC ................................................ A61K 41/0028  
See application file for complete search history.

(56) References Cited

U.S. PATENT DOCUMENTS 5,437,274 A     8/1995     Khoobehi et al.  
5,686,113 A     11/1997     Speaker et al.  
(Continued)

FOREIGN PATENT DOCUMENTS

CN     102977294 B    *    7/2014  
WO     WO-2016207296 A1    *    12/2016       ............. A61K 31/37

OTHER PUBLICATIONS

English Translation of CN102977294B. Obtained from Google Patents at https://patents.google.com/patent/CN102977294B/en?oq=pnipaam+coated+polylactic+acid on Apr. 28, 2022. Originally published in Chinese on Jul. 2, 2014, pp. 1-7. (Year: 2014).*

(Continued)

*Primary Examiner* — Isaac Shomer

(57) ABSTRACT

A method of macular disease treatment (500) may include introducing nanocapsules into a body of a patient (502). The nanocapsules may be introduced such that the nanocapsules circulate through at least a portion of a body of the patient. A therapeutic substance and a colorant may be encapsulated into the nanocapsules. After a portion of the nanocapsules enters choroidal neovessels of an eye of the patient, the method may include emitting a pulsed laser radiation through a pupil of the eye (504). Additionally, after a portion of the nanocapsules enters choroidal neovessels of an eye of the patient, the method may include heating the portion of the nanocapsules present in the eye (506) such that at least a portion of the nanocapsules transfer phase and release the therapeutic substance.

9 Claims, 8 Drawing Sheets

(51) Int. Cl.

| | |
|---|---|
| *A61N 5/06* | (2006.01) |
| *A61N 5/067* | (2006.01) |
| *A61K 9/00* | (2006.01) |
| *A61K 38/36* | (2006.01) |
| *A61K 45/06* | (2006.01) |

(52) U.S. Cl.
CPC ............ *A61K 9/5138* (2013.01); *A61K 38/36* (2013.01); *A61K 45/06* (2013.01); *A61N 5/062* (2013.01); *A61N 5/067* (2021.08)

(56) References Cited

U.S. PATENT DOCUMENTS

| | | | |
|---|---|---|---|
| 7,115,120 | B2 | 10/2006 | Lin |
| 7,836,894 | B2 | 11/2010 | Brinkmann et al. |
| 2002/0127224 | A1 | 9/2002 | Chen |
| 2003/0163175 | A1 | 8/2003 | Shaw |
| 2006/0127481 | A1* | 6/2006 | Kataoka ............... A61K 9/1075 514/410 |
| 2007/0117750 | A1 | 5/2007 | Abdulrazik |
| 2008/0145405 | A1 | 6/2008 | Kunzler et al. |
| 2014/0148792 | A1* | 5/2014 | Coppeta ............... A61F 9/0017 604/93.01 |
| 2015/0119792 | A1* | 4/2015 | Almutairi ............... A61K 9/513 604/20 |
| 2019/0105200 | A1* | 4/2019 | Hipsley ................... A61F 9/008 |

OTHER PUBLICATIONS

Hyun Jun Cho, Minsub Chung, and Min Suk Shim. "Engineered photo-responsive materials for near-infrared-triggered drug delivery." Journal of Industrial and Engineering Chemistry, vol. 31, 2015, pp. 15-25. (Year: 2015).*

Joanne D. Du, Wye-Khay Fong, Suzanne Caliph, and Ben J. Boyd. "Lipid-based drug delivery systems in the treatment of wet age-related macular degeneration." Drug Delivery and Translational Research, vol. 6. 2016, pp. 781-792. (Year: 2016).*

Qian Peng, Asta Juzeniene, Jiyao Chen, Lars O Svaasand, Trond Warloe, Karl-Erik Giercksky and Johan Moan. "Lasers in Medicine." Reports on Progress in Physics, vol. 71, 2008, pp. 1-28. (Year: 2008).*

Xiaohua Huang, Prashant K. Jain, Ivan H. El-Sayed, and Mostafa A. El-Sayed. "Plasmonic photothermal therapy (PPTT) using gold nanoparticles." Lasers in Medical Science, vol. 23, 2008, pp. 217-228, (Year: 2008).*

Martin A. Mainster et al. "Continuous-wave and Micropulse 577 nm Yellow Laser Photocoagulation: A Laser for All Reasons." Insert to Retina Today, Apr. 2010, pp. 1-8. (Year: 2010).*

Tatu Lajunen et al. "Light induced cytosolic drug delivery from liposomes with gold nanoparticles." Journal of Controlled Release, vol. 203, 2015, pp. 85-98. (Year: 2015).*

Tatu Lajunen et al. "Light induced cytosolic drug delivery from liposomes with gold nanoparticles." Journal of Controlled Release, vol. 203, 2015, pp. 85-98 and 29 pages of supplementary information. (Year: 2015).*

International Search Report and Written Opinion for International Application No. PCT/CN2017/097834 dated May 16, 2018, pp. 09.

Cao, Z., et al., "Synthesis of Narrowly Size-Distributed Thermosensitive Poly(N-isopropylacrylamide) Nanocapsules in Inverse Miniemulsion," Macromolecules, vol. 43, Issue 15, pp. 6353-6360 (Jul. 15, 2010).

Mora-Huertas, C.E. et al., "Polymer-based nanocapsules for drug delivery," International Journal of Pharmaceutics, vol. 385, Issues 1-2, pp. 113-142 (Jan. 29, 2010).

Occhiutto, M.L., et al., "Breakdown of the Blood-Ocular Barrier as a Strategy for the Systemic Use of Nanosystems," Pharmaceutics, vol. 4, Issue 2, pp. 252-275 (May 14, 2012).

* cited by examiner

NANOCAPSULE-BASED OCULAR THERAPY

CROSS-REFERENCE

This patent application is section 371 nationalization of PCT Application No. PCT/CN2017/097834 filed Aug. 17, 2017, which provisional is incorporated herein by specific reference in its entirety.

BACKGROUND

Unless otherwise indicated herein, the materials described herein are not prior art to the claims in the present application and are not admitted to be prior art by inclusion in this section.

Ocular disease may result in loss of vision or reduction in quality of vision of a patient. Diabetic macular edema (DME), age-related macular degeneration (AMD), ocular disease, hypoprothrombinemia, and central serous chorioretinopathy (CSC) are examples of ocular disease. In some treatment systems, there may be no effective method of ocular-specific drug delivery other than injection into the eye. Injection into the eye may result in discomfort of the patient.

SUMMARY

Techniques described herein generally relate to therapeutic radiation treatment systems and methods.

In an example embodiment, a method of macular disease treatment may include introducing nanocapsules into a body of a patient. The nanocapsules may be introduced such that the nanocapsules circulate through at least a portion of a body of the patient. A therapeutic substance and a colorant may be encapsulated into the nanocapsules. After a portion of the nanocapsules enters choroidal neovessels of an eye of the patient, the method may include emitting a pulsed laser radiation through a pupil of the eye. After a portion of the nanocapsules enters choroidal neovessels of an eye of the patient, the method may include heating the portion of the nanocapsules present in the eye such that at least a portion of the nanocapsules transition phase and release the therapeutic substance.

In another example embodiment, a nanocapsule may include a core, a shell, and a therapeutic substance. The core may be constructed of a hydrophobic polymer. The shell may be constructed of a temperature-sensitive hydrogel. The therapeutic substance may be encapsulated within the core. The shell may be configured such that the therapeutic substance is retained within the shell during circulation in a body of a patient. The therapeutic substance may be released from the core in response to absorption of laser radiation.

In yet another example embodiment, an ocular therapy system may include a radiation source and nanocapsules. The radiation source may be configured to emit a pulsed laser through a pupil of an eye of a patient. The nanocapsules may each include a core, a shell, a therapeutic substance, and a colorant. The core may be constructed of a hydrophobic polymer. The shell may be constructed of a temperature-sensitive hydrogel. The therapeutic substance may be encapsulated within the core. The colorant may be encapsulated within the core. The colorant may imitate a color of a retinal colorant epithelial (RPE) cell. The temperature-sensitive hydrogel may have a critical solution temperature (CST) below which the shell prevents biological interaction and above which the shell becomes hydrophobic.

In some embodiments, a method of macular disease treatment can include: introducing nanocapsules into a body of a patient such that at least a portion of the nanocapsules enter an eye of the patient, wherein the nanocapsules encapsulate a therapeutic substance and a colorant; emitting a pulsed laser radiation through a pupil of the eye; and—heating the portion of the nanocapsules present in the eye with the pulsed laser radiation such that at least a portion of the nanocapsules release the therapeutic substance. In some aspects, the introduction of the nanocapsules into the body includes injecting the nanocapsules intravenously.

In some embodiments, each nanocapsule includes: a shell that comprises a temperature-sensitive hydrogel; a core that comprises a hydrophobic polymer; the therapeutic substance is encapsulated within the core; and—the colorant is encapsulated within the core.

In some embodiments, the temperature-sensitive hydrogel of the nanocapsule has a critical solution temperature (CST) such that the temperature-sensitive hydrogel undergoes a phase transition. The CST can be between about 38° C. and about 48° C. to cause a phase transition, or about 45° C. to cause a phase transition.

In some embodiments, the colorant has a different optical absorption range from retinal cells of the eye. Accordingly, the method further includes absorbing a first portion of the therapeutic radiation by the nanocapsules and absorbing a second portion of the therapeutic radiation by a retinal pigment epithelial (RPE) cell.

In some embodiments, the method includes milting the pulsed laser radiation in accordance with at least one of: emitting the pulsed laser radiation for a time in a range from about 0.5 microseconds (µs) to about 2.0 µs; or emitting the pulsed laser radiation at a wavelength in a range of about 500 nanometers (nm) and about 600 nm.

In some embodiments, the method includes emitting the pulsed laser radiation in accordance with at least one of: emitting the pulsed laser radiation for a time of about 1.7 microseconds (µs), and emitting the pulsed laser radiation at a wavelength of about 527 nanometers (nm).

In some embodiments, a nanocapsule can include: a core having a hydrophobic polymer and a shell having a temperature-sensitive hydrogel; and a therapeutic substance encapsulated within the core. In some aspects, the shell is configured to retain the therapeutic substance within the core during circulation in a body of a patient; and the shell is configured to undergo a phase transition and release the therapeutic substance from the core in response to absorption of laser radiation. In some aspects, the colorant is encapsulated in at least one of the core or shell. The colorant can have at least one of a color or optical absorption range that absorbs a wavelength of laser radiation.

In some embodiments, the shell has CST where the shell undergoes a phase transition and becomes hydrophobic. The shell can have a CST that is between about 38° C. and about 48° C. In some aspects, the shell has a CST that is 45° C. The temperature-sensitive hydrogel can include an acrylamide polymer, such as poly (N-isopropyl acrylamide) (PNIPAAm).

In some embodiments, the colorant comprises a color of a retinal pigment epithelial (RPE) cell. In some aspects, the colorant has an optical absorption within an absorption range of a retinal pigment epithelial (RPE) cell.

In some embodiments, an ocular therapy system can include a radiation source configured to emit a pulsed laser radiation through a pupil of an eye of a patient and nanocapsules that include: a core having a hydrophobic polymer; a shell having a temperature-sensitive hydrogel; a therapeutic substance encapsulated within the core; and a colorant encapsulated within at least one of the core or shell that has a color of a retinal colorant epithelial cell; and the shell is configured to undergo a phase transition and release the therapeutic substance from the core in response to absorption of laser radiation from the radiation source.

BRIEF DESCRIPTION OF THE FIGURES

The foregoing and following information, as well as other features of this disclosure, will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings:

DETAILED DESCRIPTION

Figure 1A:
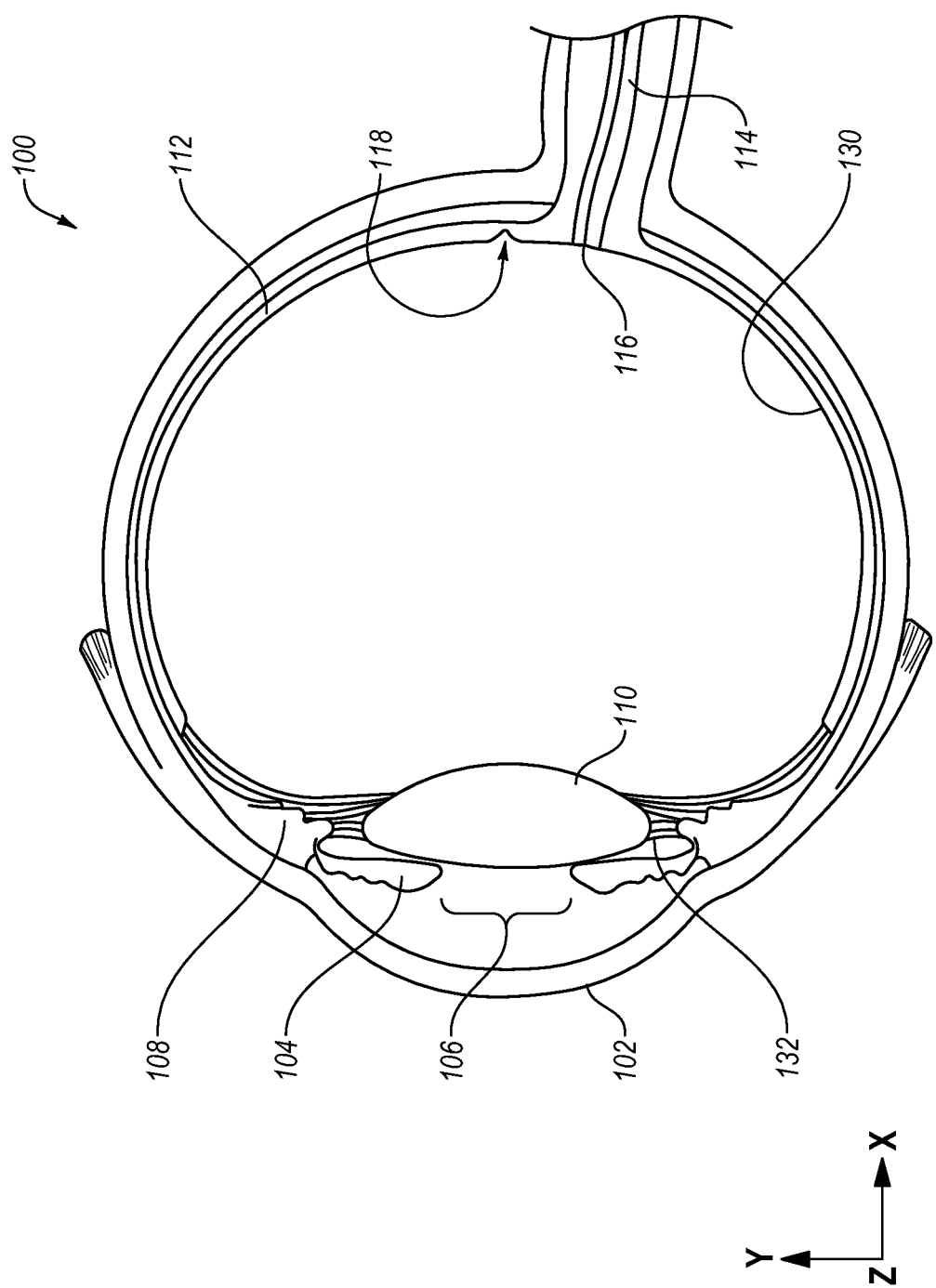
FIG. 1A is a cross-sectional view of an example human eye (hereinafter "eye")

This disclosure is generally drawn to methods, apparatus, systems, devices, and computer program products related to therapeutic radiation dosimetry.

In this detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

Ocular disease such as diabetic macular edema (DME), age-related macular degeneration (AMD), central serous chorioretinopathy (CSC), ocular cancers, and hypoprothrombinemia may result in vision impairment or vision loss. Some treatments of the ocular diseases involve direct delivery processes of therapeutic substances to the eye. The direct delivery processes may include surgical placement and injection. The direct delivery processes may cause discomfort to patients.

Accordingly, in some embodiments described herein, a system is described that may be configured to treat one or more ocular diseases. Treatment of the ocular disease may involve introduction of nanocapsules into a body of a patient. The nanocapsules have encapsulated therein a therapeutic substance. The nanocapsules may then be exposed to a pulsed laser radiation. The pulsed laser radiation may be emitted by a laser-based ophthalmological treatment system or another ocular treatment system. The pulsed laser radiation may be emitted through a pupil of the eye and to the nanocapsules. The pulsed laser radiation may be emitted after the nanocapsules have traveled to the eye via a circulatory system.

The nanocapsule may include a shell made from polymer or a polymeric membrane. The shell may surround or envelope a core. The scale of the nanocapsules is the nanoscale. Exposure to the pulsed laser radiation may result in heating of a portion of the nanocapsules. The heating of the nanocapsules may transition phase of the portion of the nanocapsules and release the therapeutic substance. The released therapeutic substance may treat the ocular disease.

A colorant may be encapsulated into the nanocapsules. The colorant may be configured such that the pulsed laser radiation interacts with the nanocapsules, which may increase energy transfer to the nanocapsules.

FIG. 1A is a cross-sectional view of an example human eye (hereinafter "eye") 100. The eye 100 may include a cornea 102, an iris 104, a pupil 106, a ciliary body 108, a lens 110, a retina 112, a fundus 130, and an optic nerve 114. The retina 112 generally includes a light-sensitive layer of tissue upon which optics of the eye 100 project an image of the visual world external to the eye 100. Through a series of chemical and electrical events, nerve impulses may be triggered in response to light striking the retina 112. The nerve impulses may be processed in vision centers of the brain such that the visual world may be perceived by a person.

The fundus 130 of the eye 100 includes an interior surface of the eye 100 opposite the lens 110. The fundus 130 may include a portion of the retina 112. The retina 112 includes an optic disc 116, sometimes referred to as the "blind spot." The retina 112 may also include a macula 118. The macula 118 may be separated from the optic disc 116 on the retina 112. The eye 100 may rotate in a socket to view an object. Rotation of the eye 100 may orient the pupil 106 and the retina 112 to receive light from the object. The pupil 106 allows the light to enter the eye 100. When the eye 100 moves, the pupil 106 and the retina 112 may move in the y-direction and/or the z-direction of an arbitrarily defined Cartesian coordinate system of FIG. 1A. Additionally, in response to the light, a diameter of the pupil 106 may change.

Figure 1B:
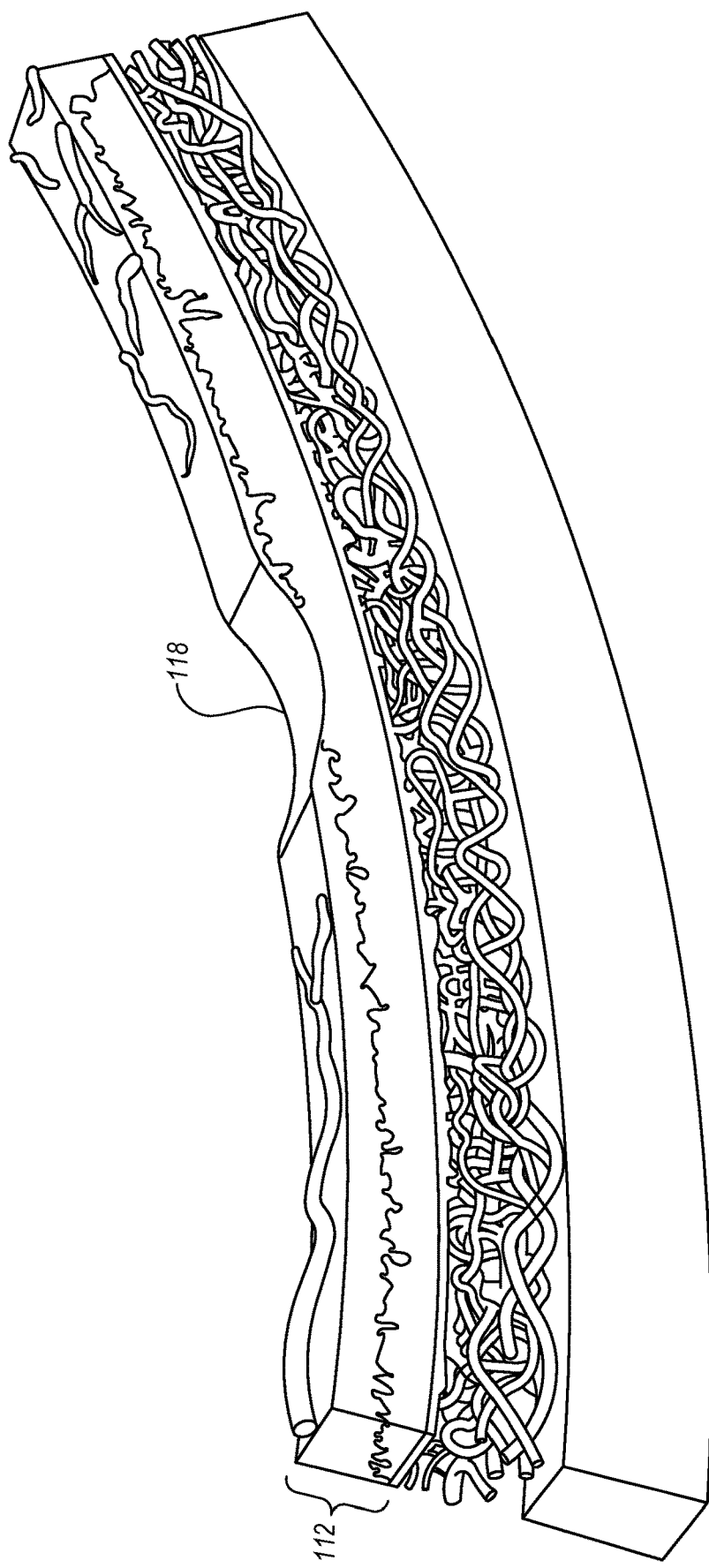
FIG. 1B is a cross-sectional perspective view of a portion of a retina and a macula of FIG. 1B.

FIG. 1B is a cross-sectional perspective view of a portion of the retina 112 and the macula 118 of FIG. 1A.

Figure 1C:
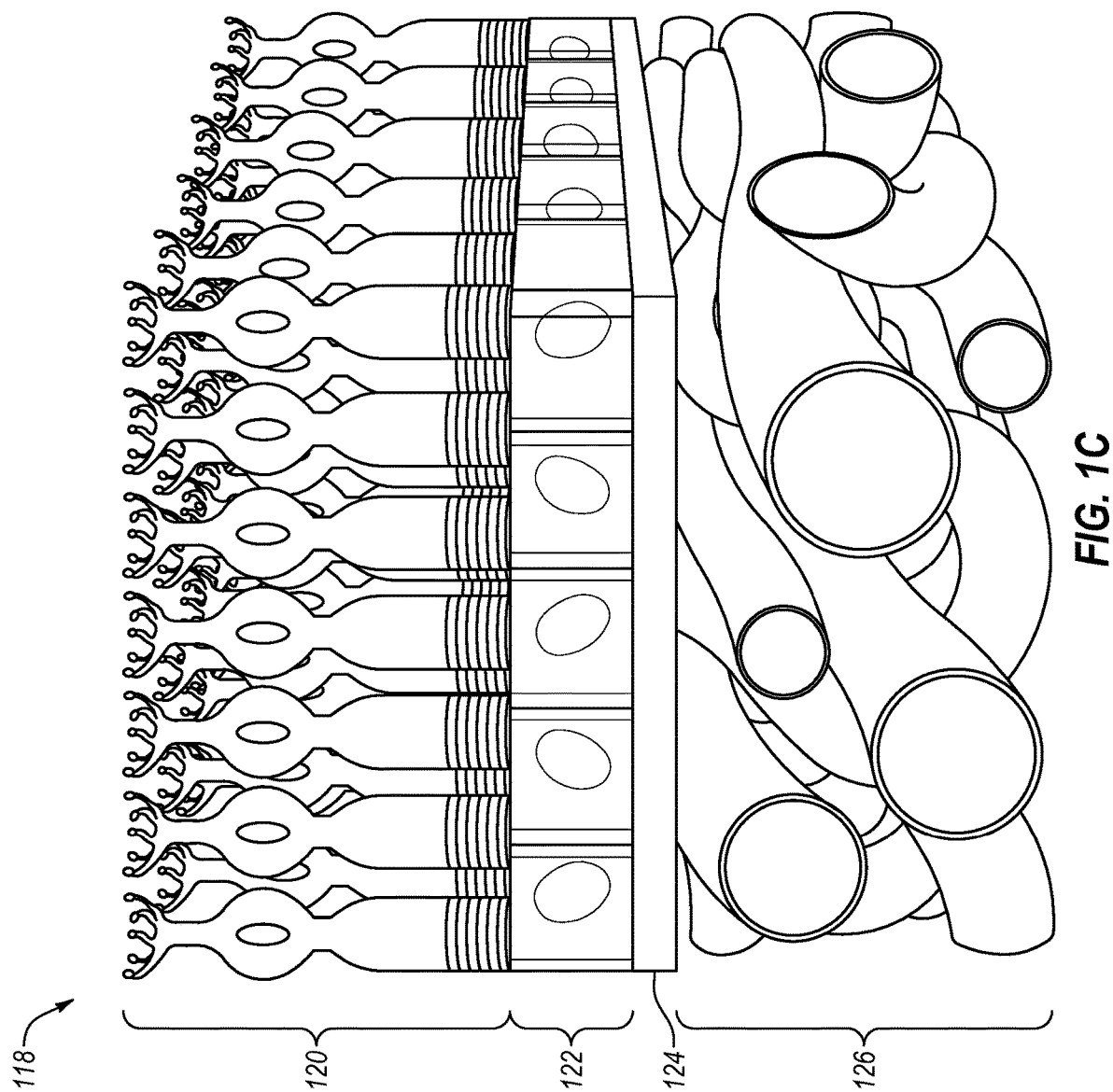
FIG. 1C is a cross-sectional perspective view of a portion of the macula of FIG. 1B.

FIG. 1C is a cross-sectional perspective view of a portion of the macula 118 of FIG. 1B. FIG. 1C depicts various layers that may make up the macula 118, including photoreceptors 120, retinal pigment epithelial (RPE) cells 122, Bruch's membrane 124, and choroid 126. The macula 118 may have a relatively high concentration of photoreceptors 120 compared to the rest of the retina 112 and without blood vessels, for central and/or high-resolution vision. The RPE cells 122 may nourish the photoreceptors 120 by supplying nutrients from the choroid 126 and transporting extracellular material out through the Bruch's membrane 124.

Various conditions may adversely affect vision in the eye 100. For instance, with reference to FIGS. 1A-1C, AMD may involve degradation of the RPE cells 122 in the macula 118.

In dry AMD, degraded RPE cells 122 may fail to transport extracellular material which may then begin to build up ("Drusen") in between the Bruch's membrane 124 and the RPE cells 122. The Drusen may interfere with the supply of nutrients to the photoreceptors 120, which can lead to vision loss. In wet AMD, new blood vessels (neovascularization) may grow from the choroid 126 and penetrate the Bruch's membrane 124 and the RPE cells 122 to supply nutrients to the photoreceptors 120. The new blood vessels may be weak and prone to bleeding and leakage, which may result in blood and protein leakages, which in turn may damage the photoreceptors 120 and fuel rapid vision loss.

Another condition that may adversely affect vision in the eye 100 may be DME. In more detail, persons with diabetes may experience a slowing of metabolism over time, which may reduce the ability of retinal vessels to deliver enough nutrients, which in turn may induce neovascularization. Fluid leakage from the neovascularization may cause the retina 112 to swell, causing vision loss. Another condition that may adversely affect vision in the eye 100 may be CSC. In CSC, leakage of fluid accumulates under the central macula 118, which may result in blurred or distorted vision, which may progressively decline with each recurrence. Ocular cancers may also develop in the eye 100. There are a number of different cancers that may affect the eye 100. For example, ocular cancers may include an ocular melanoma that develops from cells called melanocytes. Ocular melanomas may start in an area of the eye called the uvea, which includes the iris 104, the choroid 126, and ciliary body 108. Additionally, hypoprothrombinemia may affect the eye 100. A common symptom of hypoprothrombinemia is a tendency to prolonged bleeding.

Some embodiments described herein include a laser-based ophthalmological treatment system that includes a radiation source configured to emit therapeutic radiation to activate nanocapsules to treat AMD, DME, CSC, hypoprothrombinemia, ocular cancers, and/or other conditions of the eye 100.

Figure 2:
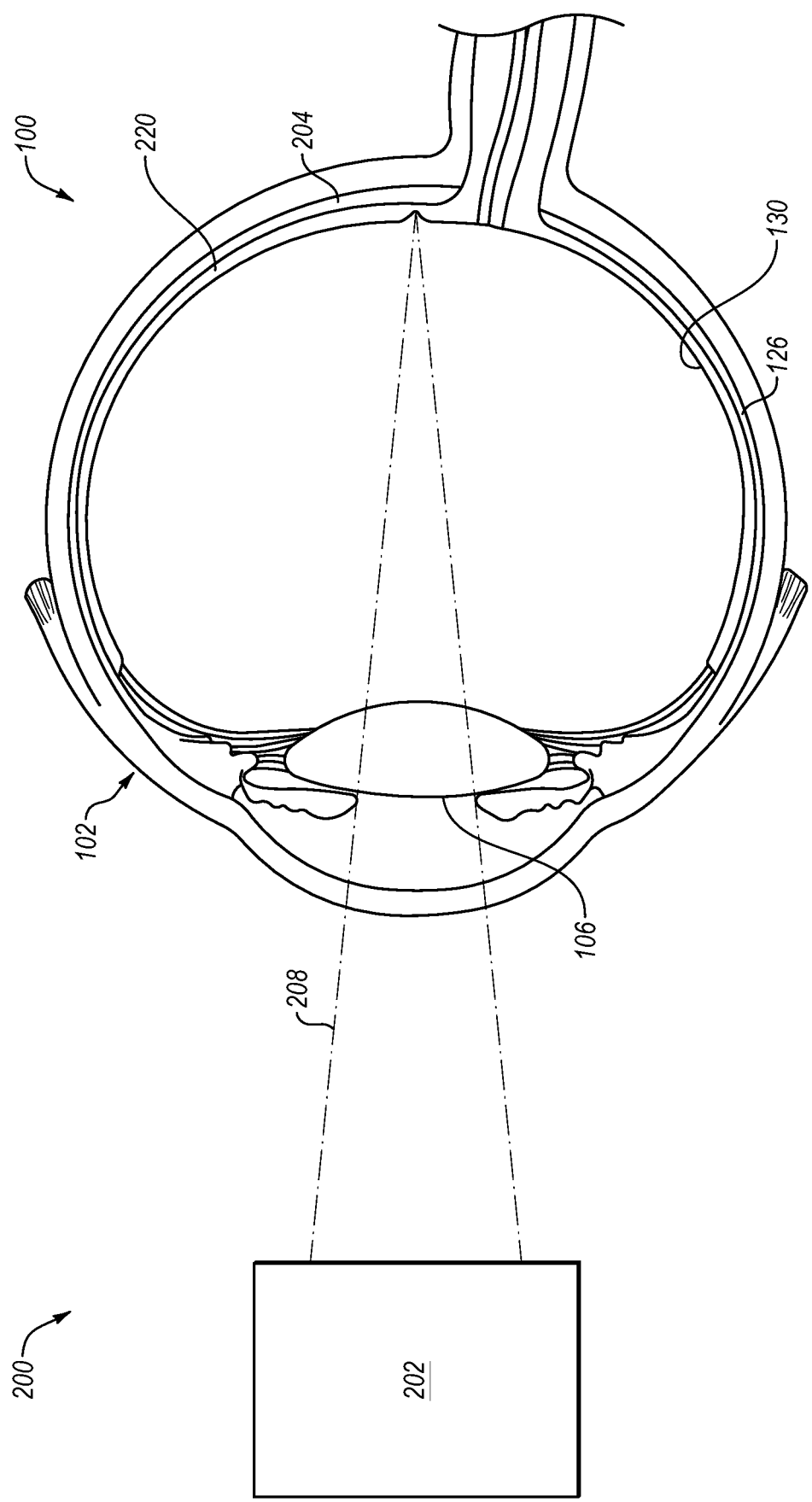
FIG. 2 is a block diagram of an example ocular therapy system.

FIG. 2 is a block diagram of an ocular therapy system 200. The ocular therapy system 200 is shown with the eye 100 of FIG. 1. The ocular therapy system 200 may be configured to deliver a therapeutic substance to the eye 100 and to activate an ocular therapy in a localized area within the eye 100.

The ocular therapy system 200 may include a radiation source 202. The radiation source 202 may be configured to emit a laser radiation 208. The laser radiation 208 may be a pulsed laser radiation or another suitable type of laser radiation. The laser radiation 208 may be emitted through the pupil 106 of the eye 100. The laser radiation 208 may be used to activate at least a portion of nanocapsules 204. Activation of the nanocapsules 204 may result from exposure to the laser radiation 208. The activation may change the nanocapsules 204 such that a therapeutic substance is released from the nanocapsules 204. The therapeutic substance may treat a diseased portion of the eye 100. For instance, the nanocapsules 204 may be in the choroid 126 of the eye 100 at least temporarily. While the nanocapsules 204 are in the choroid 126, the laser radiation 208 may be directed to the choroid 126 to treat a diseased portion of the choroid 126.

In some embodiments, the nanocapsules 204 may be introduced into a body of the patient. The nanocapsules 204 may be introduced into the body such that the nanocapsules circulate in the circulatory system of the patient. For instance, the nanocapsules 204 may be injected intravenously into the patient. In embodiments in which the nanocapsules 204 are injected into the intravenously, the nanocapsules 204 may be suspended or otherwise retained in a fluid such as saline.

Additionally, in some embodiments, a surface or some portion thereof of the nanocapsules 204 may be modified to help concentration of the nanocapsules 204 in a target area. For example, the surface of the nanocapsules 204 may include vascular endothelial growth factor (VEGF) and/or arginylglycylaspartic acid (RGD) peptide, which may help concentrate the nanocapsules 204 in the eye.

After the nanocapsules 204 are introduced into the body, the nanocapsules 204 may travel or circulate throughout the body (e.g., via the circulatory system). As the nanocapsules 204 travel through the body, some portion of the nanocapsules 204 may not be activated. For example, the nanocapsules 204 may be configured to remain inactivated unless the nanocapsules 204 are exposed to the laser radiation 208. For example, the nanocapsules 204 may be constructed of a polymer. The polymer may be inert chemically and may be stable in a temperature range of the body (e.g., below about 30 degrees Celsius). The nanocapsules 204 that remain inactivated may be metabolized and pass out of the body without being activated.

The particular metabolic process by which the nanocapsules 204 that are not activated pass out of the body may depend on the structure and/or composition of the nanocapsule 204. For instance, in embodiments in which the nanocapsules 204 include nitrogen-substituted acrylamide polymers, poly (N-isopropyl acrylamide) (PNIPAAm), the nanocapsules 204 may not degenerate in vivo. Instead, a macrophage in a mononuclear phagocyte system (MPS) may obtain the nanocapsules 204. The macrophage may keep the original form of the nanocapsules 204 unchanged in the liver. Alternatively, in embodiments in which the nanocapsules 204 include a degradable material, such as Dipalmitoylphosphatidylcholine+poly(ethyleneglycol)-(1,2-Distearoyl-sn-glycero-3-phosphoethanolamine) (DPPC+PEG-DSPE), the nanocapsules 204 may be collected by macrophages and then be delivered to the liver. The nanocapsules 204 may be degraded by liver enzymes in the liver.

A portion of the nanocapsules 204 may travel to choroidal neovessels 220 of the choroid 126. For instance, after a period of time that may be related to the arm-retina circulation time, the nanocapsules 204 may travel to the choroidal neovessels 220 of the choroid 126. The arm-retina circulation time, in some humans, may be in a range of about 11 to about 13 seconds. The nanocapsules 204 may circulate multiple times through the choroidal neovessels 220 for a circulation time. The circulation time may extend from the injection into the body until the nanocapsules 204 are metabolized in the body. In some circumstance, the circulation time may be about 30 minutes. After the nanocapsules 204 are present in the choroidal neovessels 220, the laser radiation 208 may be emitted to activate the nanocapsules 204.

The nanocapsules 204 may be configured such that presence of the nanocapsules 204 does not interfere with the function (e.g., clog) of the choroidal neovessels 220. For example, a size of the nanocapsules 204 may be configured such that the nanocapsules 204 do not become lodged in the choroidal neovessels 220. As discussed elsewhere in the present disclosure, the nanocapsules 204 may include a diameter that is about an order of magnitude less than a red blood cell, which enables circulation of the nanocapsules 204 in the choroidal neovessels 220.

The nanocapsules 204 may each include a core and a shell. The therapeutic substance may be encapsulated within the core. For example, the therapeutic substance may be encapsulated using nanoprecipitation, emulsion-diffusion, double emulsification, or another suitable encapsulation process. Some details of encapsulation of the therapeutic substance in the core are provided in C. E. Mora-Huertas et. al., POLYMER-BASED NANOCAPSULES FOR DRUG DELIVERY, Int'l J. of Pharmaceutics, 385 (2010) 113-142, which is incorporated herein by reference in its entirety. In some embodiments, the therapeutic substance may include an ocular medication. For example, the therapeutic substance may include a cytotoxic substance, a prothrombin, an anti-vascular endothelial growth factor (anti-VEGF) drug, or another ocular medication.

Additionally, a colorant may be encapsulated within the core and/or the shell. The colorant may be encapsulated by one or more of the encapsulation processes above (e.g., nanoprecipitation, emulsion-diffusion, double emulsification, etc.). In some embodiments, the colorant imitates a color of the RPE cells 122. For example, the colorant may be brownish in color. The radiation source 202 may be configured to emit a laser radiation 208. The laser radiation 208 may be configured to be absorbed by the colorant. For instance, the wavelength and/or the frequency of the laser radiation 208 may be configured to be absorbed by the colorant.

In some embodiments, the colorant may be different from one or more cell types of the eye 100. In these and other embodiments, the colorant may accordingly absorb energy of the laser radiation 208 in a higher portion than the one or more cell types that may surround the nanocapsules 204.

The core may be constructed of a polymer. The polymer may be configured such that it is inert or substantially inert in the body. In some embodiments, the core may be constructed of a hydrophobic polymer.

The shell may surround the core. For example, the core may have a spherical, spheroid, ellipsoid, or an oblate spheroid shape. Similarly, the shell may have a spherical, spheroid, an ellipsoid, or an oblate-spheroid shape that envelopes the core.

The shell may have a critical solution temperature (CST). Below the CST, the shell may prevent biological interaction. Above the CST, the shell may enable the release of the therapeutic substance from the core into the eye 100. Accordingly, in some embodiments of the ocular therapy system 200, prior to exposure to the laser radiation 208, the therapeutic substance is retained within the shell during circulation in the body. In response to exposure to the laser radiation 208, the shell may become biologically active and enable release of the therapeutic substance. For instance, in response to exposure to the laser radiation 208, the shell may become hydrophobic. An example of the CST may be between about thirty-eight degrees Celsius (C) and about forty-eight degrees C.

The radiation source 202 may be configured to emit the laser radiation 208 through the pupil 106 of the eye 100 of a patient. The laser radiation 208 may be emitted in pulses. For instance, the laser radiation 208 may be emitted for a time between about 0.5 microseconds (µs) to about 2.0 µs or about 1.7 µs in some embodiments. The laser radiation 208 may be emitted in one or more pulses. The laser radiation 208 may have a wavelength in a range of about 500 nanometers (nm) and about 600 nm and may have a wavelength of about 527 nm in some embodiments.

Figure 3:
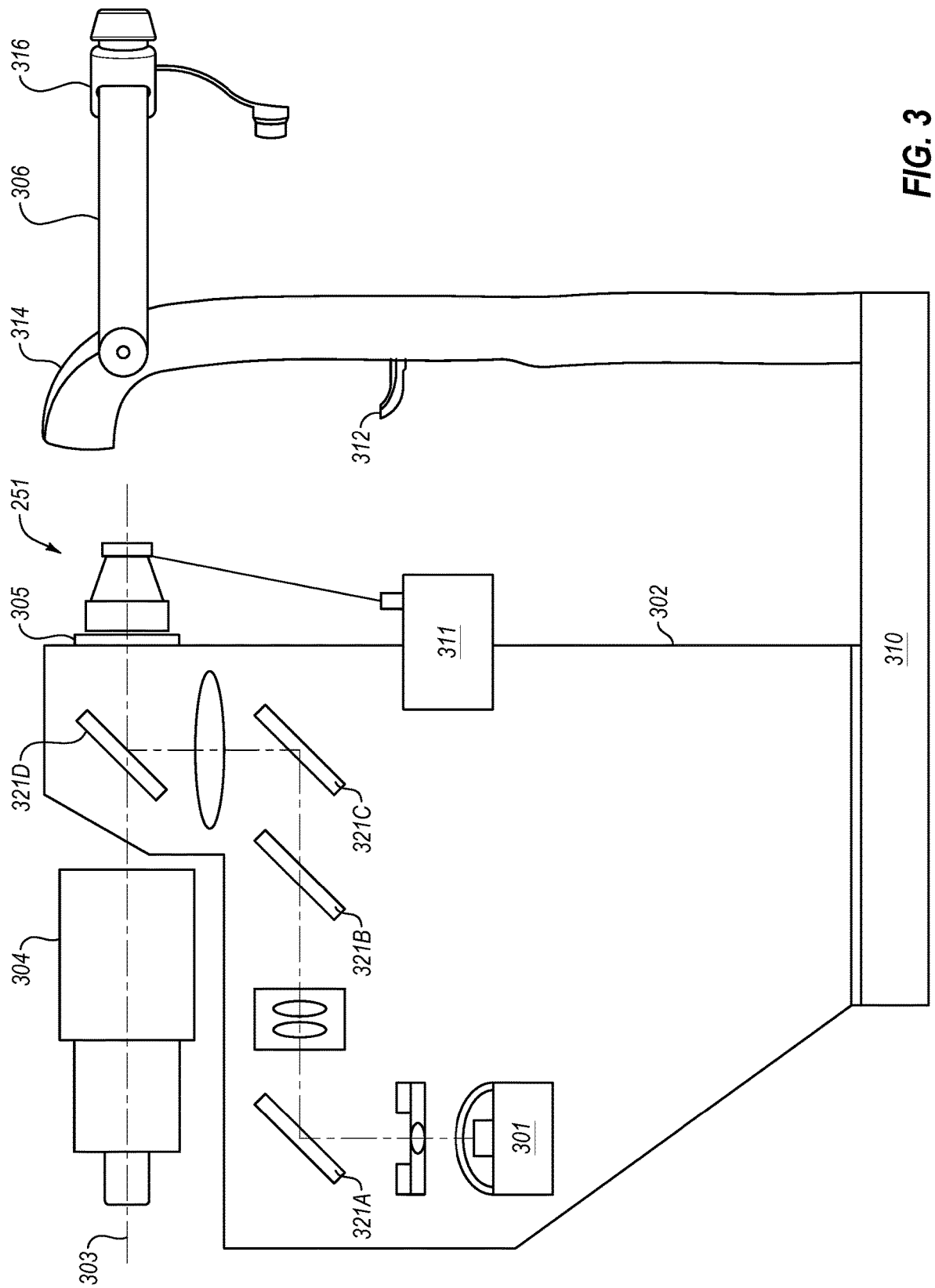
FIG. 3 illustrates an example laser-based ophthalmological surgical system that may be implemented in the ocular therapy system of FIG. 2.

FIG. 3 is a block diagram of an example laser-based ophthalmological treatment system 300 (hereinafter, "treatment system 300"), arranged in accordance with at least one embodiment described herein. FIG. 3 is a section view of the treatment system 300. The treatment system 300 may also be configured to administer laser-based treatment of an ocular disease. For example, the treatment system 300 may be configured to activate nanocapsules that are introduced into an eye of a patient. Activation of the nanocapsules may result in the release of a therapeutic substance of the nanocapsules into the eye or tissues therein.

The laser-based treatment may include a pulsed laser radiation that is emitted from a radiation source 301. The radiation source 301 may correspond with and may be substantially similar to the radiation source 202. For example, in some embodiments, the treatment system 300 may be configured to pulse laser radiation into an eye of the patient. The pulsed laser radiation may be configured to transfer energy or a higher portion of the energy to a substance that has a particular color or has a color within a particular wavelength range. For example, the pulsed laser radiation may be configured to transfer energy to a particular colorant of a nanocapsule, to RPE cells, or other cells in a diseased portion of the eye.

The treatment system 300 may include a device housing 302, a microscope 304, and a head fixation assembly 306. As shown in FIG. 3, the device housing 302, the microscope 304, and the head fixation assembly 306 may be visible. The device housing 302 may be positioned apart from the head fixation assembly 306 and may be fixed relative to the head fixation assembly 306. For instance, in some embodiments, the device housing 302 may be secured to a base 310 at a first location. The head fixation assembly 306 may also be secured to the base 310 at a second location. The head fixation assembly 306 may accordingly be fixed relative to the device housing 302. In some embodiments, the head fixation assembly 306 may be secured directly to the device housing 302 or otherwise fixed relative to the device housing 302.

The device housing 302 may surround or partially surround components of the treatment system 300. For instance, the device housing 302 may partially surround the microscope 304. A first portion of the microscope 304 into which a healthcare provider looks may be external to the device housing 302. A second portion of the microscope 304 (e.g., lenses, focus elements, etc.) may be positioned within the device housing 302. The microscope 304 may be positioned in an optical path 303 to allow an operator to view the eye of the patient. The optical path 303 may be aligned with a center or a near center of a pupil of a patient during emission of the pulsed laser radiation. The pulsed laser radiation may be emitted along the optical path 303. Generally, administration of the pulsed laser radiation, on the pupil of a patient is aligned along the optical path 303.

The head fixation assembly 306 may be configured to position and to retain a head of the patient relative to the device housing 302. Accordingly, once fixed within the head fixation assembly 306, the head of the patient may be positioned and retained relative to the device housing 302 and/or the microscope 304.

In some embodiments, the head fixation assembly 306 may include a jaw portion 312, a forehead rest 314, and a fixing band 316. A jaw of the patient may be placed in the jaw portion 312 and a forehead of the patient may be placed against the forehead rest 314. The fixing band 316 may be placed and tightened around the head to fix the head in the head fixation assembly 306.

FIG. 3 depicts an example arrangement of components that may be positioned within the device housing 302. In FIG. 3, the treatment system 300 is depicted with a contact lens assembly 351. The contact lens assembly 351 may be placed in contact with the eye of the patient in the head fixation assembly 306. The contact lens assembly 351 may be placed directly on a cornea of the eye.

The radiation source 301 may be configured to emit or transmit the pulsed laser radiation. The pulsed laser radiation may be emitted at least partially along the optical path 303. The pulsed laser radiation may be emitted through the contact lens assembly 351 and to the eye of the patient. The pulsed laser radiation may be configured to specifically target a substance of a particular color. For instance, the pulsed laser radiation may be configured to specifically target a colorant of a nanocapsule introduced to the eye and/or a layer of the retina of the eye such as the RPE cells (e.g., the RPE cells 122 of the retina 112 of FIGS. 1A-1C).

In an example embodiment, the pulsed laser radiation is administered in pulses with a pulse duration of between half a microsecond to several microseconds, such as 1.7 microseconds. The administration of the therapeutic radiation may be periodic in some embodiments, with a pulse frequency in a range from 50 hertz (Hz) to 200 Hz (corresponding to a period in a range of 0.02 seconds to 0.005 seconds), such as about 100 Hz (corresponding to a period of 0.01 seconds). For instance, multiple radiation pulses, each with a pulse duration of 1.7 microseconds, may be sequentially administered with a pulse frequency of 100 Hz.

In some embodiments, a pulse type and/or pulse control of the therapeutic radiation may be in a range of about 500 nanometers (nm) to about 600 nm or about 527 nm. Additionally or alternatively, the therapeutic radiation may be emitted in multiple pulses. For instance, the therapeutic radiation may be emitted in sets of between about 9 and about 20 pulses or about 15 pulses. In some other embodiments, the therapeutic radiation may include operating characteristics similar to those described in U.S. Pat. Nos. 7,115,120 and 7,836,894, which are incorporated herein by reference in their entireties.

The administration of pulses transfers energy from the pulsed laser radiation to nanocapsules introduced into the eye of the patient. For example, the nanocapsules may be present in choroidal neovessels. The pulsed laser radiation may be emitted into the eye and directed to the choroidal neovessels. Energy of the pulsed laser radiation may transfer to the nanocapsules, which may heat the nanocapsules. In response, the nanocapsules may transition phase and release a therapeutic substance of the nanocapsules. The therapeutic substance may then affect cells of the eye.

Some embodiments described herein may start administration of the pulsed laser radiation at a relatively low exposure that ramps up with each successive pulse. In some embodiments, the pulsed laser radiation may ramp up until a real-time feedback indicates a threshold exposure has been reached. In an example, the first pulse of pulsed laser radiation may be at about 50% of a relatively high energy level, such as a maximum energy level. More generally, the first pulse may be at a relatively low energy level, and each successively administered pulse of the pulsed laser radiation may be increased compared to the preceding pulse. The amount of increase from pulse to pulse may be fixed or variable. For instance, in an example embodiment, the amount of increase from pulse to pulse may be fixed at 5% of the relatively high energy level.

The radiation source 301 may be positioned outside of the optical path 303. The pulsed laser radiation may be redirected or transmitted by one or more of the optical elements 321A-321D to the optical path 303. In other embodiment, the radiation source 301 may be positioned on the optical path 303. Although the radiation source 301 is shown in the therapeutic system of FIG. 3, the radiation source 301 may be implemented in other suitable systems such as the ocular therapy system 200 of FIG. 2.

Prior to emission of the pulsed laser radiation by the radiation source 301, the head of the patient may be fixed in the head fixation assembly 306. For instance, the patient may place their jaw against the jaw portion 312 and may place their forehead against the forehead rest 314. The fixing band 316 may be placed around the head and tightened to fix the head relative to the head fixation assembly 306.

With the head of the patient fixed in the head fixation assembly 306, a portion of the fundus of the eye may be aligned with the optical path 303 of the treatment system 300. For example, the choroidal neovessels of the patient may be aligned with the optical path 303. Following the alignment and following the nanocapsules reaching the choroidal neovessels, the pulsed laser radiation may be emitted along the optical path 303. The nanocapsules may then be activated by the pulsed laser radiation. Activation of the nanocapsules may result in release of a therapeutic substance, which may treat a diseased portion of the eye.

The contact lens assembly 351 may be positioned between the device housing 302 and the head fixation assembly 306. The contact lens assembly 351 may be placed directly on the eye of a patient. In some embodiments, the contact lens assembly 351 may be held in a hand of a healthcare provider during diagnosis and/or treatment of the eye of a patient. For instance, the healthcare provider may be positioned such that the healthcare provider may view and/or operate the microscope 304. With the head of the patient fixed in the head fixation assembly 306, the healthcare provider may hold the contact lens assembly 351 against the cornea of the eye of the patient. When the contact lens assembly 351 is placed on the cornea of the eye, the contact lens assembly 351 may be oriented along the optical path 303.

In some embodiments, the system may include a patient contact lens assembly retainer 305. The patient contact lens assembly retainer 305 may be coupled to the device housing 302. The patient contact lens assembly retainer 305 may be configured to selectively retain the contact lens assembly 351 relative to the device housing 302. For instance, instead of or in addition to the contact lens assembly 351 being held by the healthcare provider, the contact lens assembly 351 may be retained in the patient contact lens assembly retainer 305.

Figure 4:
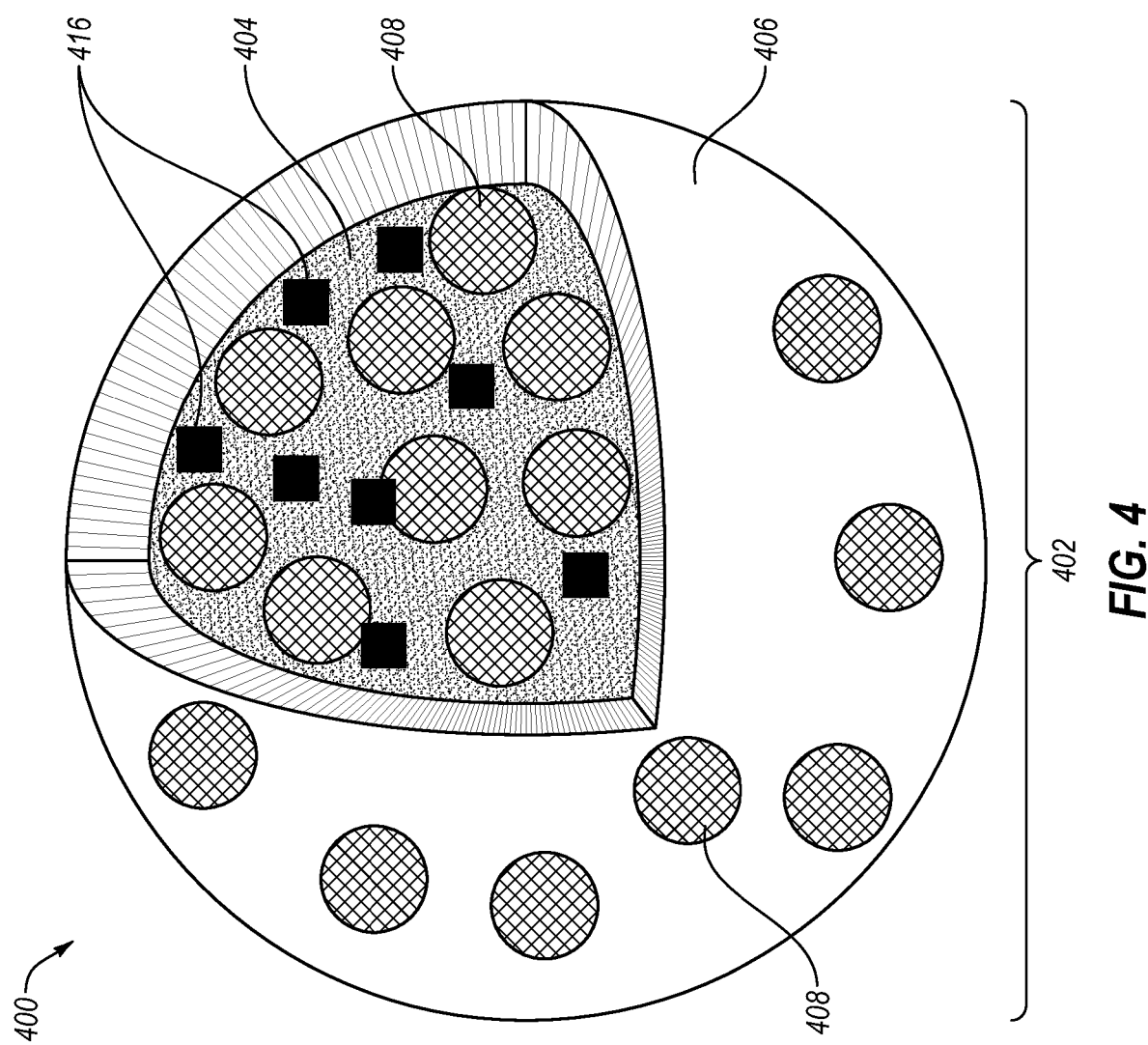
FIG. 4 depicts a block diagram of an example nanocapsule that may be implemented in the ocular therapy system of FIG. 2.

FIG. 4 is a block diagram of an example nanocapsule 400 according to some embodiments of the present disclosure. The nanocapsule 400 of FIG. 4 may be substantially similar to and correspond to the nanocapsules 204 of FIG. 2. The nanocapsule 400 may be configured for delivery of a therapeutic substance 416 and for controlled release or activation by a radiation source such as the radiation sources 301 of FIG. 3 or 202 of FIG. 2. For example, the nanocapsule 400 may be configured to release the therapeutic substance 416 in response to exposure to a pulsed laser radiation (e.g., the laser radiation 208 of FIG. 2).

The nanocapsule 400 may be substantially spherical. The nanocapsule 400 may include a diameter 402 that enables the nanocapsule to pass through cell membranes. For instance, the diameter 402 may be in a range of between about 10 nanometers (nm) to about 1000 nm. In application, the nanocapsule 400 may be one of a set of nanocapsules. The set of nanocapsules may include multiple thousands or millions of nanocapsules. The nanocapsules in the set of nanocapsules may have a mean size. The mean size, in some embodiments, may be in a range of about 50 nm to about 500 nm. Additionally, in some implementations, the mean size may be in a range of about 150 nm to about 250 nm or in a range of about 160 nm to about 250 nm.

The nanocapsule 400 may include a shell 406. The shell 406 may surround and enclose a core 404. The shell 406 may be configured to not chemically react with the core 404. Additionally, the shell 406 may be configured to not chemically or biologically react with a body of a patient. Accordingly, as the nanocapsule 400 circulates through the body of the patient, the shell 406 prevents or substantially prevents interaction between the core 404 and the body and the shell 406 does not react with the core 404.

A material of the shell 406 may have a CST. The material may be selected such that the CST is in a particular range. For example, the material may be selected such that the shell 406 is not affected by normal temperatures in a body of a patient. Additionally, the material may be selected such that the shell 406 is affected by exposure to a pulsed laser radiation. For example, the shell 406 may include a CST of between about thirty-eight degrees Celsius (C) and about forty-eight degrees C. or about 45 degrees C. in some embodiments. Accordingly, in these and other embodiments, when exposure to the pulsed laser radiation raises the temperature of the shell 406 to about 45 degrees C., the shell 406 may enable release of the therapeutic substance 416 from the core 404.

In some embodiments, the shell 406 may be constructed at least partially of a hydrogel. The hydrogel may be temperature-sensitive. For instance, one or more chemical or material properties of the hydrogel may change based on a temperature of the shell 406. Some suitable hydrogels may include nitrogen-substituted acrylamide polymers, poly (N-isopropyl acrylamide) (PNIPAAm), or another suitable material.

The core 404 may encapsulate the therapeutic substance 416. Some examples of encapsulation of the therapeutic substance 416 are elsewhere in the present disclosure. The therapeutic substance 416 may include an ocular medication. The specific ocular medication may depend on the type of medical condition the nanocapsule 400 is configured to treat.

For example, the nanocapsule 400 may be configured to treat dry (atrophic) or wet (neovascular) forms of macular degeneration. In these and other embodiments, the therapeutic substance 416 may include an anti-vascular endothelial growth factor (anti-VEGF) drug. The anti VEGF drug may reduce formation of abnormal blood vessels involved in the macular degeneration. In some therapies, the nanocapsules 400, and the anti-VEGF is injected into the eye. The use of the nanocapsule 400 may enable the patients suffering from the macular degeneration from having the anti-VEGF being injected into the eye and associated risks. Instead, using an ocular therapy system (e.g., 200 of FIG. 2) or the treatment system 300, the patient may be treated for the macular degeneration using a radiation source that activates the nanocapsules 400.

Additionally, the nanocapsules 400 may be configured to treat an ocular cancer such as an uveal or a choroidal melanoma or another type of ocular cancer. In these and other embodiments, the therapeutic substance 416 may include a cytotoxic substance. After the therapeutic substance 416 is released, the cytotoxic substance may be metabolized by the cancerous cells, which may be toxic to the cancerous cells. To treat ocular cancers, some treatments involve surgery, radiotherapy, and chemotherapy. The use of nanocapsules 400 may help avoid or supplement these treatment options.

Additionally still, the nanocapsules 400 may be configured to treat hypoprothrombinemia, which may result in a tendency to have prolonged bleeding. In these and other embodiments, the therapeutic substance 416 may include a prothrombin. The prothrombin may promote thrombin production in the eye.

The core 404 may be constructed of a polymer, which may be in a liquid or gel phase. The polymer may be configured such that it is inert or substantially inert in the body. In some embodiments, the core 404 may be constructed of a hydrophobic polymer. Accordingly, after the nanocapsule 400 is activated, the therapeutic substance 416 may be released. The remaining portions of the core 404 may be metabolized by the body.

A colorant 408 may be encapsulated within the core 404 and/or the shell 406. The colorant 408 may be encapsulated by one or more of the encapsulation processes described elsewhere in this disclosure. As described above, the colorant 408 may be configured to interact with a pulsed laser radiation. For example, the pulsed laser radiation may heat to a greater extent substances and objects of a particular color. The colorant 408 may be configured such that the pulsed laser radiation heats the nanocapsule 400 to a greater extent than other cells in the eye or that otherwise surround the nanocapsule 400. For example, the colorant 408 may imitate a color of a cell type of the eye (e.g., the RPE cells) or may differentiate from a color of a cell type of the eye.

Figure 5:
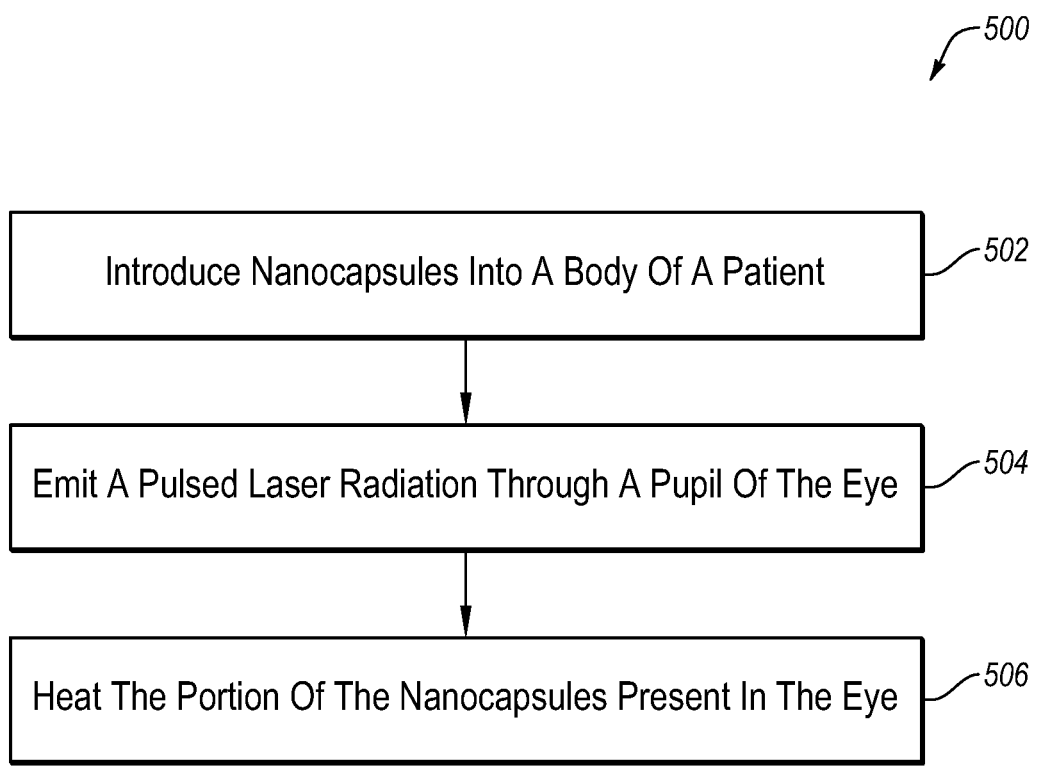
FIG. 5 illustrates a flow diagram of an example method of a macular disease treatment.

FIG. 5 is a flow diagram of an example method 500 of macular disease treatment, arranged in accordance with at least some embodiments described herein.

The method 500 may be performed, in whole or in part, in the ocular therapy system 200 and/or in other systems and configurations. Alternatively or additionally, the method 500 may be implemented at least partially by a processor device that performs or controls performance of one or more of the operations of the method 500. For instance, a computer (such as the computing device 600 of FIG. 6) or another processor device may be communicatively coupled to the ocular therapy system 200 and may execute software or other computer-readable instructions accessible to the computer, e.g., stored on a non-transitory computer-readable medium accessible to the computer, to perform or control the ocular therapy system 200 to perform the method 500 or a portion thereof.

The method 500 may include one or more of blocks 502, 504, and 506. Although illustrated as discrete blocks, various blocks may be divided into additional blocks, supplemented with additional blocks, combined into fewer blocks, or eliminated, depending on the particular implementation. The method 500 may begin at block 502.

At block 502 ("Introduce Nanocapsules Into A Body Of A Patient"), nanocapsules may be introduced into a body of a patient. The nanocapsules may be introduced such that the nanocapsules circulate through at least a portion of a body of the patient. For instance, the introducing the nanocapsules may include injecting the nanocapsules intravenously.

In some embodiments, the nanocapsules may include a core. The core may be constructed at least partially of a hydrophobic polymer. The nanocapsules may include a shell. The shell may be constructed of a temperature-sensitive hydrogel. In some embodiments, the temperature-sensitive hydrogel may be an acrylamide polymer or a nitrogen-substituted acrylamide polymer or poly (N-isopropyl acrylamide) (PNIPAAm). The temperature-sensitive hydrogel may have a critical solution temperature (CST). At the CST, the temperature-sensitive hydrogel may undergo a phase transition. In some embodiments, the CST may be between about thirty-eight degrees Celsius (C) and about forty-eight degrees C. For instance, the CST may be about forty-five degrees C.

In some embodiments, a therapeutic substance and a colorant may be encapsulated into the nanocapsules. The therapeutic substance may be encapsulated within the core. The therapeutic substance may include an ocular medication. Some examples of the ocular medication may include a cytotoxic substance, a prothrombin, an anti-vascular endothelial growth factor (anti-VEGF) drug, or another ocular medication.

The colorant may be encapsulated within the core. The colorant may be configured to imitate a color of a retinal colorant epithelial (RPE) cell. The colorant has an optical absorption within an absorption range of the RPE cell. The colorant may be configured such that energy of the pulsed laser radiation is absorbed by the colorant. Alternatively, the colorant may be configured to have a different absorption from retinal cells of the eye. In these and other embodiments, the colorant may be configured such that a first portion of the therapeutic radiation is absorbed by the nanocapsules and a second portion of the therapeutic radiation is absorbed by the RPE cell. The first portion may be greater than the second portion. Block 502 may be followed by block 504.

At block 504 ("Emit A Pulsed Laser Radiation Through A Pupil Of The Eye"), a pulsed laser radiation may be emitted through a pupil of the eye. For example, the pulsed laser radiation may be emitted after a portion of the nanocapsules enters choroidal neovessels of an eye of the patient. The pulsed laser radiation may be emitted for a time. The time may be in a range from about 0.5 microseconds (µs) to about 2.0 µs. For instance, the pulsed laser radiation may be emitted for a time of about 1.7 (µs). The pulsed laser radiation may have a wavelength in a range of about 500 nanometers (nm) and about 600 nm. For instance, the pulsed laser radiation may have a wavelength of about 527 nm. Block 504 may be followed by block 506.

At block 506 ("Heat The Portion Of The Nanocapsules Present In The Eye"), the portion of the nanocapsules present in the eye may be heated. The portion of the nanocapsules may be heated such that at least a portion of the nanocapsules transition phase and release the therapeutic substance. The portion of the nanocapsules may be heated after a portion of the nanocapsules enters choroidal neovessels of an eye of the patient.

One skilled in the art will appreciate that, for this and other procedures and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the disclosed embodiments.

Figure 6:
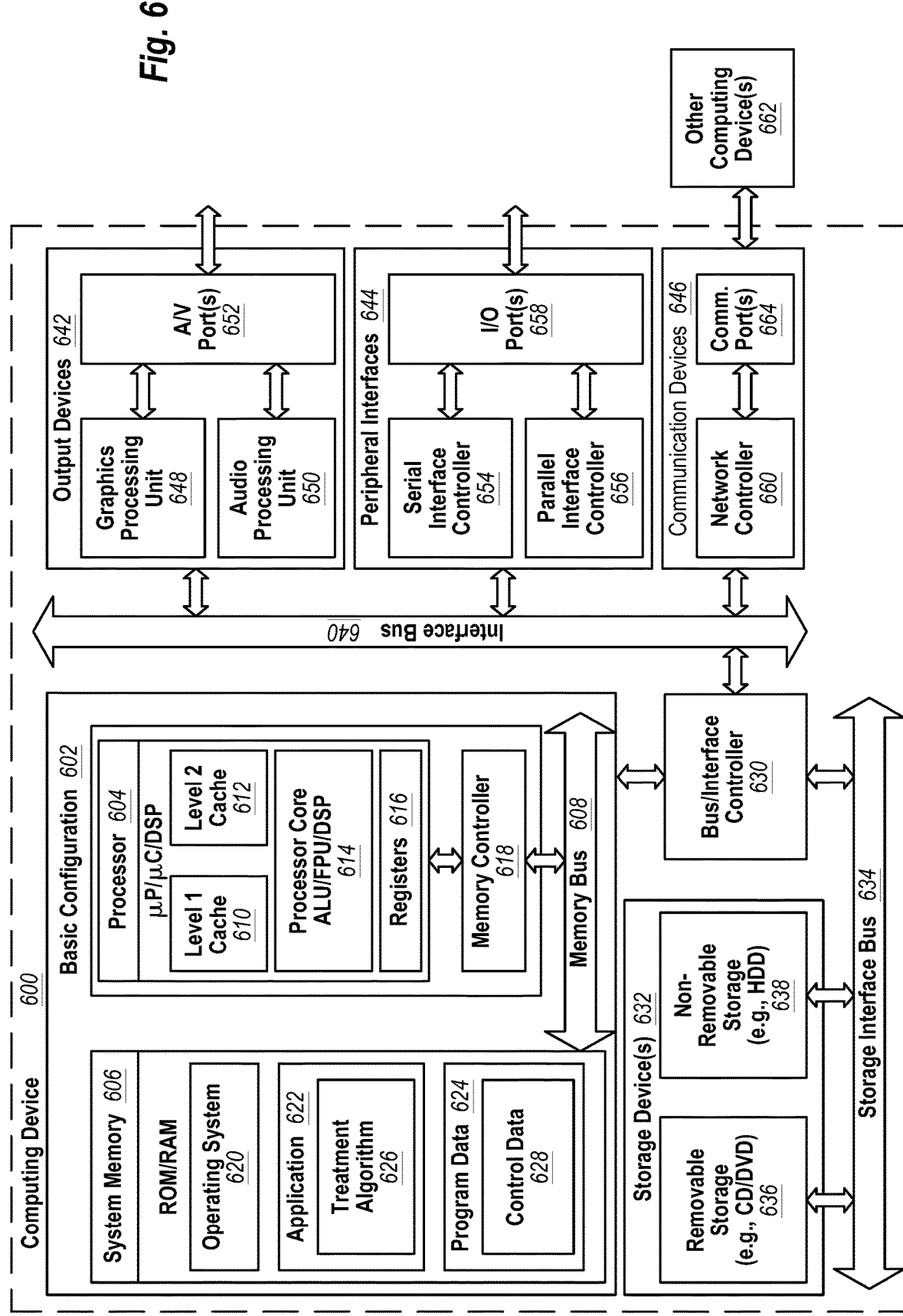
FIG. 6 is a block diagram of an example computing device, all arranged in accordance with at least one embodiment of the present disclosure.

FIG. 6 illustrates a block diagram of an example computing device 600, in accordance with at least one embodiment of the present disclosure. The computing device 600 may be used in some embodiments to perform or control performance of one or more of the methods and/or operations described herein. For instance, the computing device 600 may be communicatively coupled to and/or included in the treatment system 300 of FIG. 3 or in the ocular therapy system 200 of FIG. 2 to perform or control performance of the method 500 of FIG. 5. In a basic configuration 602, the computing device 600 typically includes one or more processors 604 and a system memory 606. A memory bus 608 may be used for communicating between the processor 604 and the system memory 606.

Depending on the desired configuration, the processor 604 may be of any type including, such as a microprocessor (µP), a microcontroller (µC), a digital signal processor (DSP), or any combination thereof. The processor 604 may include one or more levels of caching, such as a level one cache 610 and a level two cache 612, a processor core 614, and registers 616. The processor core 614 may include an arithmetic logic unit (ALU), a floating point unit (FPU), a digital signal processing core (DSP Core), or any combination thereof. An example memory controller 618 may also be used with the processor 604, or in some implementations, the memory controller 618 may be an internal part of the processor 604. Depending on the desired configuration, the system memory 606 may be of any type, such as volatile memory (such as RAM), non-volatile memory (such as ROM, flash memory, or the like), or any combination thereof. The system memory 606 may include an operating system 620, one or more applications 622, and program data 624. The application 622 may include a treatment algorithm 626. The treatment algorithm 626 may be configured to control a radiation source relative to nanocapsules in an eye of a patient. The program data 624 may include radiation source control data (in FIG. 6 "control data 628") such as aiming, alignment, and targeting information. In some embodiments, the application 622 may be arranged to operate with the program data 624 on the operating system 620 to perform one or more of the methods and/or operations described herein, including those described with respect to FIG. 5.

The computing device 600 may include additional features or functionality, and additional interfaces to facilitate communications between the basic configuration 602 and any other devices and interfaces. For example, a bus/interface controller 630 may be used to facilitate communications between the basic configuration 602 and one or more data storage devices 632 via a storage interface bus 634. The data storage devices 632 may include removable storage devices 636, non-removable storage devices 638, or a combination thereof. Examples of removable storage and non-removable storage devices include magnetic disk devices such as flexible disk drives and hard-disk drives (HDDs), optical disk drives such as compact disk (CD) drives or digital versatile disk (DVD) drives, solid state drives (SSDs), and tape drives to name a few. Example computer storage media may include volatile and non-volatile, removable and non-removable media implemented in any method or technology for storage of information, such as computer-readable instructions, data structures, program modules, or other data.

The system memory 606, the removable storage devices 636, and the non-removable storage devices 638 are examples of computer storage media. Computer storage media includes, but is not limited to, RAM, ROM, EEPROM, flash memory or other memory technology, CD-ROM, digital versatile disks (DVDs) or other optical storage, magnetic cassettes, magnetic tape, magnetic disk storage or other magnetic storage devices, or any other medium which may be used to store the desired information and which may be accessed by the computing device 600. Any such computer storage media may be part of the computing device 600.

The computing device 600 may also include an interface bus 640 for facilitating communication from various interface devices (e.g., output devices 642, peripheral interfaces 644, and communication devices 646) to the basic configuration 602 via the bus/interface controller 630. The output devices 642 include a graphics processing unit 648 and an audio processing unit 650, which may be configured to communicate to various external devices such as a display or speakers via one or more A/V ports 652. The peripheral interfaces 644 include a serial interface controller 654 or a parallel interface controller 656, which may be configured to communicate with external devices such as input devices (e.g., keyboard, mouse, pen, voice input device, touch input device, and/or others), sensors, or other peripheral devices (e.g., printer, scanner, and/or others) via one or more I/O ports 658. The communication devices 646 include a network controller 660, which may be arranged to facilitate communications with one or more other computing devices 662 over a network communication link via one or more communication ports 664. The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that includes one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term "computer-readable media" as used herein may include both storage media and communication media.

The computing device 600 may be implemented as a portion of a small-form factor portable (or mobile) electronic device such as a cell phone, a personal data assistant (PDA), a personal media player device, a wireless web-watch device, a personal headset device, an application-specific device, or a hybrid device that includes any of the above functions. The computing device 600 may also be implemented as a personal computer including both laptop computer and non-laptop computer configurations.

The present disclosure is not to be limited in terms of the particular embodiments described herein, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of this disclosure. Also, the terminology used herein is for the purpose of describing particular embodiments only, and is not intended to be limiting. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that include A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that include A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

For any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, and/or others. As a non-limiting example, each range discussed herein can be readily broken down into a lower third, middle third and upper third, etc. All language such as "up to," "at least," and the like include the number recited and refer to ranges which can be subsequently broken down into sub ranges as discussed above. Finally, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, various embodiments of the present disclosure have been described herein for purposes of illustration, and various modifications may be made without departing from the scope and spirit of the present disclosure. Accordingly, the various embodiments disclosed herein are not intended to be limiting.

What is claimed is:

1. A method of delivering
a therapeutic substance to an eye of a patient the method comprising:
introducing nanocapsules into a body of the patient such that at least a portion of the nanocapsules enter an eye of the patient, wherein the nanocapsules encapsulate a therapeutic substance and a colorant; and
emitting pulsed laser radiation through a pupil of an eye of the patient;
wherein the portion of the nanocapsules present in the eye is heated by the pulsed laser radiation, thereby causing at least a portion of the nanocapsules to release the therapeutic substance in the eye,
wherein the pulsed laser radiation has a wavelength in a range of about 500 nanometers (nm) to about 600 nm.

2. The method of claim 1, wherein the introducing of the nanocapsules into the body includes injecting the nanocapsules intravenously.

3. The method of claim 1, wherein each nanocapsule includes:
a shell that comprises a temperature-sensitive hydrogel; and
a core that comprises a hydrophobic polymer,
wherein the therapeutic substance is encapsulated within the core, and
wherein the colorant is encapsulated within the core.

4. The method of claim 3, wherein the emitting of laser radiation through the pupil of an eye of the patient heats the portion of nanocapsules present in the eye to a critical solution temperature (CST) such that the temperature-sensitive hydrogel of the nanocapsule undergoes a phase transition.

5. The method of claim 4, wherein the critical solution temperature (CST) is between about 38° C. and about 48° C.

6. The method of claim 5, wherein the critical solution temperature (CST) is about 45° C.

7. The method of claim 1, wherein the colorant has a different optical absorption range from retinal cells of the eye of the patient, wherein a first portion of the pulsed laser radiation is absorbed by the nanocapsules and a second portion of the pulsed laser radiation is absorbed by retinal pigment epithelial (RPE) cells in the eye of the patient.

8. The method of claim 1,
wherein the pulsed laser radiation is emitted for a time in a range from about 0.5 microseconds (μs) to about 2.0 μs.

9. The method of claim 1,
wherein the pulsed laser radiation is emitted for a time of about 1.7 microseconds (μs), and/or
wherein the pulsed laser radiation has a wavelength of about 527 nanometers (nm).

* * * * *